United States Patent [19]

Van Gestel et al.

[11] Patent Number: 4,542,146

[45] Date of Patent: Sep. 17, 1985

[54] PROCESS FOR THE PROTECTION OF WOOD AND COATINGS AGAINST DETERIORATION BY MICROORGANISMS

[75] Inventors: Josef Van Gestel, Vosselaar; Benedikt Duytschaever, Ekeren, both of Belgium; René Muntwyler, Hofstetten; Max Schärer, Rheinfelden, both of Switzerland

[73] Assignee: Janssen Pharmaceutica N.V., Beerse, Belgium

[21] Appl. No.: 548,252

[22] Filed: Nov. 2, 1983

Related U.S. Application Data

[63] Continuation of Ser. No. 373,073, Apr. 29, 1982, abandoned, which is a continuation of Ser. No. 230,151, Jan. 30, 1981, abandoned.

[51] Int. Cl.$^4$ .............................................. A01N 43/48
[52] U.S. Cl. .................................. 514/383; 514/396; 514/397
[58] Field of Search ................... 426/269; 424/273 R, 424/341

[56] References Cited

U.S. PATENT DOCUMENTS 3,575,999  4/1971  Godefro et al. .................... 260/309
3,658,813  4/1972  Godefro et al. ................ 548/341 X
3,927,017 12/1975  Heeres et al. .................... 424/273 X
4,079,062  3/1978  Van Reet et al. ............. 260/308 R Primary Examiner—Leonard Schenkman
Attorney, Agent, or Firm—Geoffrey G. Dellenbaugh

[57] ABSTRACT

The agents protect wood and coatings against deterioration by microorganisms. The agents contain at least one compound of the formula

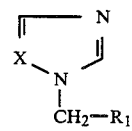

wherein X is nitrogen or a CH group and $R_1$ is a radical of the formula

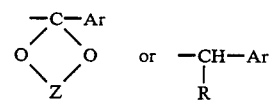

wherein Ar, R and Z are as defined in claim 1, or an acid addition salt thereof.

6 Claims, No Drawings

PROCESS FOR THE PROTECTION OF WOOD AND COATINGS AGAINST DETERIORATION BY MICROORGANISMS

This is a continuation of application Ser. No. 373,073, filed Apr. 29, 1982, now abandoned, which is a continuation of Ser. No. 230,151, filed Jan. 30, 1981, abandoned.

The present invention is concerned with agents and a process for the protection of wood and coatings against deterioration by microorganisms, as well as with antimicrobially protected wood and coatings.

It is known from the literature that many halogenated phenols are used to protect the above-mentioned substrates and as germ-killing and conservating agents. See in this connection, for example, U.S. Pat. Nos. 3,033,746, 3,062,710, 2,215,596 and 3,417,185, British Patent Specification No. 980,254, Japanese Patent Specification No. 53-26303, German Auslegeschrift No. 1,160,140, German Offenlegungsschrift No. 26 07 349 and Chemical Reviews, 28, 269 (1941). The halogenated phenols show either important lacks in their spectrum of activity, show a too high level of toxicity or an unpleasant odor, are in part difficultly accessible, require a high dose or are for other reasons not or only within limits applicable in practice. For example, pentachlorophenol, which is widely used against moulding and rotting of wood shows serious disadvantages, such as a lack of light-stability and high toxicity. See e.g. in this connection E. Graf and M. Segmuller, Textilveredlung, 12, 496 (1977) and V. Kubelka, M. Popl and J. Mosteck, Chem. Prum., 23, 304 (1973). Further, 1-(4-chlorophenoxy)-1-imidazolyl-(1)-3,3-dimethylbutan-2-one is known from German Offenlegungsschrift as an antifungal agent for the protection of materials. This agent displays however an insufficient protecting activity.

Consequently, the objective of the subject invention was to provide agents with a higher protecting activity for wood and coatings against deterioration by microorganisms while lacking the disadvantages of the above-cited compounds.

It has now been found that, in order to protect wood and coatings from deterioration by microorganisms there may successfully be used agents which comprise compounds of the formula

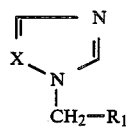
(I)

or acid addition salts thereof, wherein X is nitrogen or a CH group and $R_1$ is a radical of the formula

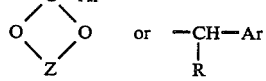

wherein Z is a group $-CH_2-CH_2-$, $-CH_2-CH_2-CH_2-$, $-CH(CH_3)-CH(CH_3)-$ or $-CH_2-CH(alkyl)-$, wherein said alkyl is a straight or branched $C_1-C_{10}$ alkyl radical; said Ar is a phenyl group which is optionally substituted with 1 to 3 halogens, $C_1-C_6$ alkyl radicals, $C_1-C_6$ alkoxy radicals, cyano-, trifluoromethyl- or nitro groups, a thienyl-, halothienyl-, naphthalenyl- or fluorenyl group; and, said R is $C_1-C_{10}$ alkyl, cycloalkyl, cycloalkyl-lower alkyl, lower alkenyl, aryl-lower alkyl, aryloxy-lower alkyl or a radical of the formula $-O-R_o$, wherein said $R_o$ is $C_1-C_{10}$ alkyl, lower alkenyl, lower alkynyl or aryl- lower alkyl, wherein said aryl radical is phenyl, naphthalenyl or substituted phenyl, wherein said substituted phenyl has 1 to 3 substituents selected from the group consisting of halo, cyano, nitro, phenyl, lower alkyl and lower alkoxy, provided that when more than one substituents are present only one thereof may be cyano, nitro or phenyl.

The agents according to the present invention are characterized by containing at least one compound of the formula I as defined above or an acid addition salt thereof.

Interesting compounds of formula (I) in accordance with the present invention are those having the formula

(II)

wherein X has the above-identified meaning and $R'_1$ is a radical of the formula

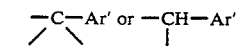

wherein Z' is a group $-CH_2-CH_2-$, $-CH_2-CH_2-CH_2-$, $-CH(CH_3)-CH_2-$, $-CH(C_2H_5)-CH_2-$, $-CH(C_3H_7)-CH_2-$, $-CH(CH_3)-CH(CH_3)-$ or $-CH(CH_3)-CH(C_2H_5)-$; Ar' is unsubstituted phenyl or phenyl substituted with 1 to 3 halogen atoms, preferably chloro atoms, $C_1-C_6$-alkyl radicals, $C_1-C_6$-alkoxy radicals, cyano or nitro groups; and R' is $C_1-C_6$-alkyl or $C_3-C_4$-alkenyloxy.

Particularly important are compounds of the formula

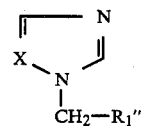
(III)

wherein X has the above-defined meaning and $R''_1$ is a radical of the formula

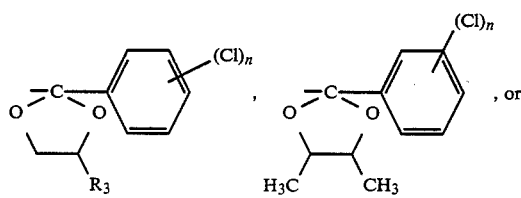

-continued

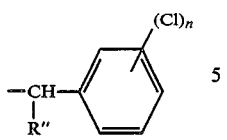
5 wherein R" is $C_1$–$C_4$ alkyl, $C_3$–$C_4$-lower alkenyloxy, $R_3$ is $C_1$–$C_3$-alkyl and n is 1 or 2.

Preferred compounds are those of the formulae

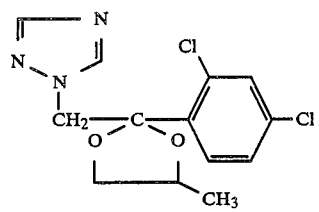 (IV)

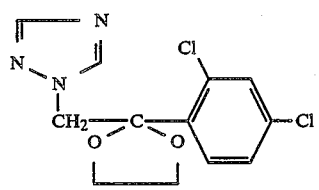 (V)

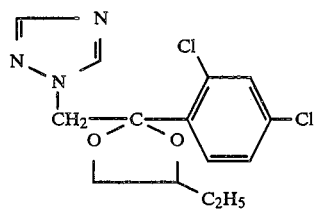 (VI)

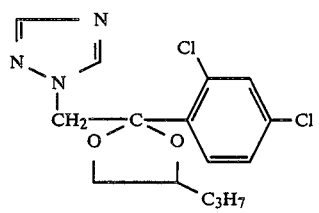 (VII)

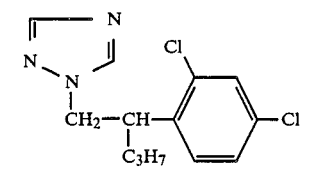 (VIII)

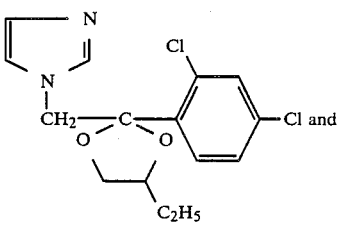 (IX)

and

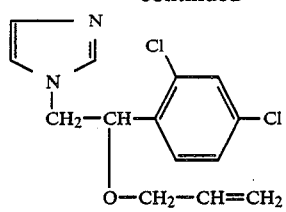 (X)

The compounds of the formulae (I) to (VIII) which may be used in accordance with the present invention may be prepared according to U.S. Pat. Nos. 3,575,999, 3,717,655, 3,636,002, 3,927,017, 4,156,008, 4,079,062, Brit. Pat. Specifications Nos. 2,026,486 and 2,027,701 and German Offenlegungsschrift No. 27 35 872.

Their good activity against human-, animal- and plant-pathogenic fungi and yeasts is indicated in the afore-cited patent specifications. As coatings within the ambit of the subject invention are considered oil paints, dispersion paints, lacquers, whitewash, and by the use of such agents obtained colored coatings, lacquer films and white coatings. As wood are considered, for example, wood products such as timber, lumber, railway sleepers, telephone poles, fences, wood coverings, wicker-work, plywood, particle board, clipboard, joinery, bridges or wood products which are generally used in housebuilding, or pulp wood used in paper manufacture.

The materials which are treated with agents according to the invention are protected from moulding, rotting loss of their useful mechanical properties such as breaking strength, resistance to shock and shearing strength; or decay of their optical or other useful properties such as the occurence of odor, staining, spot formation and dote caused by the following microorganisms: Aspergillus species, Penicillium species, Verticillium species, Alternaria species, Rhizopus species, Mucor species, Paecelomyces species, Saccharomyces species, *Trichoderma viride, Chaetomium globosum, Stachybotrys atra, Myrothecium verrucaria, Oospora lactis* and other woodrot and wood decay fungi. Special emphasis should be led on the good activity against moulds such as *Aspergillus niger, Penicillium funiculosum, Trichoderma viride, Alternaria alternata*, fungi such as *Chaetomium globosum, Trychophyton mentagrophytes, Coriolus versicolor, Coniophora cerebella, Poria monticola, Merulius (Serpula) lacrymans* and *Lenzites trabea*, and yeasts such as *Candida albicans* and Saccharomyces species.

The compounds of formula (I) may be used in agents according to the present invention on their own or in combination with appropriate carriers and/or other additives. Appropriate carriers and additives can be solid or liquid and correspond to the substances usually used in formulation techniques such as natural or regenerated inorganic substances, solvents, dispersants, emulsifiers, wetting agents, adhesion agents, thickeners or binding agents.

The compounds of formula (I) show good solubility in organic solvents and in driving gases for aerosols. The lack of color and odor of the compounds of formula (I) is in this connection of great practical value.

The invention further comprises a method of protecting wood and coatings, characterized in that compounds of formula (I) are incorporated in said wood, respectively coatings, or applied to their surface. The following agents according to the invention can be used to apply compounds of formula (I):

Solid forms: dusts and wettable powders.
Liquid forms: concentrates of the active ingredients in organic solvents or water.

In order to prepare solid forms (dusts, wettable powders) the active ingredients are mixed with the solid carriers. As carrier materials may be used, for example, kaolin, talc, bolus, löss, chalk, limestone, chalk gravel, attapulgite, dolomite, diatomaceous earth, precipitated silicic acid, earth alkaline metal silicates, sodium- and potassium aluminum silicates (felspar and mica), calcium-and magnesium sulfate, magnesium oxide, as well as their mixtures with each other.

To these mixtures there can also be added stabilizers of the active ingredient and/or non-ionically, anionically and kationically active substances that may for example improve the surface adhesiveness of the active ingredients and/or secure a better wettability (wetting agents) and dispersibility (dispersants).

The following substances may, for example, be used: olein/limestone mixture, cellulose derivatives (methylcellulose, carboxymethylcellulose), hydroxyethyleneglycolethers of mono- and dialkylphenols with 5 to 15 ethyleneoxide units per molecule and 8 to 9 carbon atoms in the alkyl radical, ligninsulfonic acids and their alkali and earth alkaline metal salts, polyethyleneglycolethers (carbowax), fatty alcohol polyglycolethers with 5 to 20 ethylene oxide units per molecule and 8 to 18 carbon atoms in the fatty alcohol part, condensation products of ethylene oxide, propylene oxide, polyvinylpyrrolidone, polyvinylalcohols, urea/formaldehyde condensation products and latex products.

In water dispersible concentrates, i.e. wettable powders, pastes and emulsifiable concentrates represent agents which can be diluted with water to any desired concentration. They consist of active ingredient, carriers, occasionally stabilizers of the active ingredient, surface active substances and anti-foam agents and occasionally solvents.

The wettable powders and pastes are obtained by mixing and grinding the active ingredients with dispersants and powdery carriers in appropriate apparatus to desired homogeneity. The same carriers as indicated above in connection with the solid forms can be used. In many cases it is advantageous to use mixtures of several carriers. As dispersants there can be used, for example anionic, kationic or non-ionic products such as, for example:

sulfated aliphatic alcohols with 8 to 18 carbon atoms in their alkyl chain; e.g., sulfated lauryl alcohol, oleyl alcohol or coconut oil;

sulfated unsaturated fatty acids or fatty acid lower alkylesters, which in the fatty radical contain 8 to 20 carbon atoms, e.g., oleic acid or ricinoleic acid and oils containing such fatty acids, e.g., ricinus oil;

alkylsulfonates the alkyl chain of which contains 8 to 20 carbon atoms, e.g., dodecylsulfonate;

alkylarylsulfonates with straight or branched alkyl chains having at least 6 carbon atoms, e.g., nonyl- or dodecylbenzenesulfonates or 3,7-diisobutylnaphthalenesulfonates;

sulfonates of polycarboxylic acid esters, e.g., dioctylsulfosuccinate;

alkali metal, ammonium or amine salts of fatty acids with 10 to 20 carbon atoms which are indicated as soaps, e.g., colophonium salts;

esters of polyalcohols, in particular mono- or diglycerides of fatty acids with 12 to 18 carbon atoms, e.g., monoglycerides of lauric, stearic or oleic acid;

acidic esters formed by the reaction of an organic dicarboxylic acid, such as, e.g., maleic, malonic, oxalic or succinic acid or preferably a polybasic anorganic acid such as phosphoric or in particular sulfuric acid, with the addition product of 1 to 60 mol of ethylene oxide and/or propylene oxide with fatty amines, fatty acids, fatty amides or fatty alcohols, each having 8 to 22 carbon atoms or with phenols which are further substituted with at least a $C_4$–$C_{10}$ alkyl group, a benzyl or phenyl group, or with three- to six-valent alkanols with 3 to 6 carbon atoms;

salts of primary, secondary and tertiary alkylamines, such as hydrochlorides, nitrates, sulfates, alkylsulfates, formiates, acetates, lactates and citrates;

salts of the reaction products of $C_{10}$–$C_{20}$ fatty acids with di- or polyamines, e.g., the chloride, sulfate, alkylsulfate, acetate, lactate and citrate of stearic acid-N-($\beta$-aminoethyl)amide or of N-oleoyl-triethylenetetramine;

salts of the reaction products of $C_{10}$–$C_{20}$ alkylhalogenides with polyalkylenepolyamines, e.g, the chloride, sulfate, alkylsulfate, acetate, lactate and citrate of N-lauryldiethylenetetramine, N-octyl-tetraethylenetetramine, N-octadecyl-triethylenetetramine or N-octadeyltrimethylenediamine;

salts of addition products of ethyleneoxide with alkylated or acylated di- or polyalkylenepolyamine, e.g., the chloride, sulfate, alkylsulfate, acetate, lactate, and citrate of N-octadecyl-N,N',N'-dioxyethyltrimethylenediamine, N-hexadecyl-N,N',N'-trioxyethylethylenediamine or N-octadecyl-N,N',N'',N''-tetraoxyethyl-diethylenediamine;

quaternized alkylaryl- or aralkylalkylamines, the nitrogen atom of which bears at least one lipophilic radical of 10 to 20 carbon atoms, e.g., lauryl-dimethyl-benzylammonium chloride, cetyldimethyl-benzylammonium chloride or hexadecyl-trimethylammonium bromide;

quaternized pyridines, the N-atom of which bears an alkyl or alkylol radical with 10 to 20 carbon atoms; e.g., laurylpyridinium chloride or sulfate, cetylpyridinium bromide, octadecyloxymethylenepyridinium chloride, stearoylaminomethylenepyridinium chloride;

quaternized imidazolines which are substituted in their 2-position which hydrophobic radicals such as alkyl- or alkylene radicals with 10 to 20 carbon atoms, alkylphenoxymethylene radicals, alkoxymethylene radicals with 10-18 carbon atoms in the alkoxy part, and alkylthiomethylene radicals with 10-18 carbon atoms in the alkylthio part, e.g., 1-hydroxyethyl-1-methyl-2-heptadecenylimidazolinium metosulfate, 1-aminoethyl-1-methyl-2-heptadecenylimidazolinium toluolsulfonate or 1-($\omega$-hydroxyethyldecaoxyethylene)-1-methyl-2-heptadecyl imidazolinium methosulfate;

quaternized benzimidazolines, e.g., N-lauryl-N-methyl-benzimidazolinium chloride;

quaternized tetrahydropyrimidines, e.g., 1-methyl-1-phenylethyldecaglycolether-2-undecyltetrahydropyridinium methosulfate;

aminooxides such as N-cetyl-N,N-dimethylaminooxide, N-octadecyl-N,N-dioxyethylaminooxide or N-stearyl-N,N-dimethylaminooxide;

addition products of preferably 5 to 80 moles alkyleneoxide, in particular ethyleneoxide, whereby individual ethyleneoxide units may be replaced by substituted epoxides, such as styryloxide and/or propyleneoxide, with higher unsaturated or saturated fatty alcohols, fatty acids, fatty amines or fatty amides with 8 to 22 carbon atoms or with phenylphenol or alkylphenols of which the alkyl radical has at least 4 carbon atoms;

condensation products of propyleneoxides, in particular ethyleneoxide and/or propyleneoxide; and reaction products of a $C_8$- to $C_{22}$-fatty acid with a primary or secondary amine which is substituted with at least one hydroxy-lower alkyl or lower alkyloxy-lower alkyl radical, or alkyleneoxide-addition products of these hydroxyalkyl radical containing reaction products, whereby the conversion is effected in such a way that the ratio of the hydroxyalkylamine to the fatty acid can be 1:1 and greater than 1, e.g., 1.1:1 to 2:1.

As anti-foaming agents there may be used, for example, silicone oils.

In order to prepare liquid forms such as solutions, emulsifiable concentrates or pastes, the active ingredients are, in the appropriate proportions, dissolved or dispersed, respectively emulsified in a solvent or dispersant, which may contain further additives, e.g., dispersants or emulsifiers.

The material to be protected which is treated with an agent according to the invention, should have a content of active ingredient of from 50 to 20,000 ppm, preferably from 2000 to 15,000 ppm. The agents according to the invention are preferably used in the form of solutions. For this purpose, one or more of the active ingredients of formula (I) are dissolved in appropriate organic solvents or solvent mixtures, occasionally in admixture with water. The content of active ingredient in the above-indicated agent is from 0.01 to 95%, preferably from 0.1 to 3% and in particular from 0.2 to 1.5% by weight.

The method according to the invention is advantageously employed for the conservation and rot-proof making of wood and coatings, whereby the active ingredients display a long lasting activity against harmful microorganisms.

Wood and coatings treated in this manner show protection from rotting and moulding caused by microorganisms.

The application forms of the active ingredients may correspond with usual formulations. Agents for the protection of wood and coatings should contain the active ingredients in a finely divided form.

For the application there may consequently be used solutions, dispersions, and emulsions of the active ingredients. Aqueous dispersions may for example be derived from pastes or concentrates and may be used in liquid form or as an aerosol.

The aqueous solutions, respectively dispersions, appropriately contain tensides, for example, anionically active substances, such as soaps and other carboxylates (e.g. alkali salts of higher fatty acids), derivatives of sulfur-oxyacids (e.g., the sodium salt of dodecylbenzenesulfonic acid, water-soluble salts of sulfuric acid, monoesters of higher alcohols or of their polyglycolethers, such as soluble salts of dodecyl-alcohol-sulfate or of dodecyl-alcohol polyglycolether-sulfate), derivatives of phosphor-oxyacids (e.g., phosphates), derivatives with an acidic (electrophilic) nitrogen in their hydrophilic radical (e.g., disulfine salts), kationically active tensides, such as amines and their salts (e.g., lauryl-diethylenetriamine), onium compounds, aminooxides, or non-ionigenic tensides, such as polyhydroxy compounds, tensides on basis of mono- or polysaccharides, higher acetylene glycols, polyglycolethers (e.g., polyglycolethers of higher fatty alcohols, polyglycolethers of higher-alkyl-substituted phenols). The treatment is appropriately carried out at temperatures from 10 to 100° C., for example, from b 10° to 70° C., preferably at about room temperature.

In view of their good solubility in organic solvents the active substances are also well suited for application in non-aqueous mediums. The materials to be protected can thereby easily be impregnated with the solutions. As organic solvents there may be used aliphatic and aromatic hydrocarbons, their chlorinated derivatives, acid amides, mineral oils, alcohols, ethers, glycolethers, such as, for example, methylenechloride, propylene glycol, methoxyethanol, ethoxyethanol, N,N-dimethylformamide on their own or as mixtures with each other, to which there may be added dispersants (e.g., emulsifiers such as sulfurated ricinus oil, fatty alcohol sulfates etc.) and/or other additives.

Compositions for treatment contain, depending on their purpose of use, from 0.1 to 50 g, preferably from 1 to 30 g of active substance per liter. By combining the subject compounds with surface-active, in particular wash-active substances there are obtained detergents with excellent activity against microorganisms, in particular fungi.

Said detergents can occur in any desired form, e.g., liquid, pasty, solid, flocky or granular. For this purpose, the active substances can be incorporated in aqueous formulations which contain one, or a mixture of more of the above tensides.

Their antimicrobial activity is fully retained thereby. The content of active ingredient in detergents, calculated by weight, is in general from 0.1 to 20%, mostly from 0.1 to 3%. Aqueous preparations of such detergents, which contain the active substances can, for example, be used for the antimicrobial treatment of wood and coatings.

The method according to the invention can further be used to protect the most different surfaces from deterioration by microorganisms. With the method of the invention there can also be achieved protection of containers in which any technical formulations are stored, of floors, walls and devices of stables, abattoirs, fruit cellars, egg incubators and the like which are fouled by organic materials.

The concerned devices, respectively surfaces are, depending on their shape, sprayed, brushed, dipped or steeped with an aqueous or organic solution, respectively dispersion of the active substance. As organic solvents there may, for example, be cited water-immiscible solvents such as, lower alcohols (e.g., ethanol, methanol), ethylene glycolmonomethylether or -monoethylether.

Preferably such an amount of the agent according to the invention is applied that the device contains, after the application, about 0.01 to 50 $g/m^2$ of the active substance.

The compounds of formula I are also suited for the protection of non-living organic materials such as refining agents. By incorporation in waxes and polishes there are obtained agents with antimicrobial action for the treatment of floors and furniture.

In the method of the invention, the active substances can also be used in combination with other antimicrobial agents, whereby an increased activity is often achieved. As antimicrobial agents, which may be used in combination with the compounds of formula I there may be considered products of the following classes:

Phenol derivatives such as 3,5-dichlorophenol, 2,5-dichlorophenol, 3,5-dibromophenol, 2,5-dibromophenol, 2,5-(resp. 3,5)-dichloro-4-bromophenol, 3,4,5-trichlorophenol, chlorinated hydroxydiphenylethers such as, for example, 2-hydroxy-3,2',4'-trichlorodiphenylether, phenylphenol, 4-chloro-2-phenylphenol, 4-chloro-2-benzylphenol, dichlorophene, hexachlorophene; aldehydes such as formaldehyde, glutatraldehyde, salicylaldehyde; alcohols such as phenoxyethanol; antimicrobially active carboxylic acids and their derivatives; organometallic compounds such as tributyltin compounds; iodine compounds such as iodophores, iodonium compounds; mono-, di- and polyamines such as dodecylamine or 1,10-di(n-heptyl)-1,10-diaminodecane; quaternary ammonium compounds such as benzyl-dimethyldodecylammonium chloride, dimethyldodecylammonium chloride, benzyl-di(2-hydroxyethyl)dodecylammoniumchloride; sulfonium- and phosphonium compounds; mercapto compounds as well as their alkali, earth alkaline and heavy metal salts such as 2-mercaptopyridine-N-oxide and its sodium and zinc salt, 3-mercaptopyridazin-2-oxide, 2-mercaptoquinoxaline-1-oxide, 2-mercapto-quinoxaline-di-N-oxide, as well as the symmetrical disulfides of said mercapto compounds; ureas such as tribromo- or trichlorocarbanilide, dichloro-trifluoromethyl-diphenylurea; tribromosalicylanilide; 2-bromo-2-nitro-1,3-dihydroxypropane; dichlorobenzoxazolon; chlorohexidine; isothia- and benzisothiazolone derivatives.

EXAMPLE I

Testing of fungicidal activity of the active substances by the agarincorporation test:

Of the compounds of formula (I) there is made each time a 5% stock solution in ethyleneglycol monomethylether. From this stock solution there is prepared a dilution series wherein the concentrations differ each time by a factor of 10. 0.3 ml of the thus obtained solutions are brought into sterile Petri dishes and mixed with 15 ml of hot liquid nutrient medium (mycophilagar). The nutrient mediums then contain 1000, 100, 10, 1 and 0.1 ppm of the active substance. After solidification of the plates there is dropped thereon with a Pasteur pipette or an inoculation device a germ suspension of *Aspergillus niger* ATCC 6275. The incubation time is 3 to 4 days at 28° C. Thereafter it is stated at which concentration of the active substance growth of the germs can still be observed. The compounds tested show a good activity against Aspergillus niger.

EXAMPLE II

Of the compounds of formula (I) there is made each time a 5% stock solution in ethyleneglycolmonomethylether. From this stock solution there is prepared a dilution series wherein the concentrations differ each time by a factor of 10. 0.3 ml of the thus obtained solutions are brought into sterile Petri dishes and mixt with 15 ml of hot liquid nutrient medium (yeast-malt-agar; oaks-malt-agar; Sabouraud-maltose-agar). The nutrient medium then contains 1000, 100, 10, 1 or 0.1 ppm of active substance. After solidification of the plates there is dropped thereon with a Pasteur pipette or an inoculation device a germ suspension of the following organisms:

Poria placenta EMPA 229
Serpula lacrymans EMPA 342
Coniophora puteana EMPA 62
Glucophyllum trabeum EMPA 100
Aureobasideum pullulans EMPA 316
Sclerophoma pityophila EMPA 315

The incubation time is 3 to 4 days at 28° C. Thereafter it is stated at which concentration of the active substance growth of the germs can still be observed. The compounds tested show a good fungistatic activity against these test fungi.

EXAMPLE III

Emulsifiable concentrates: The following substances are used to prepare a 25% emulsifiable concentrate:
  25 parts of active ingredient
  2.5 parts of epoxidized vegetable oil
  10 parts of an alkylarylsulfonate/fatty alcohol-polyglycolether mixture
  5 parts of N,N-dimethylformamide
  57.5 parts of xylene From such concentrates there can be prepared emulsions with any desired concentration by dilution with water.

EXAMPLE IV

An oil-soluble concentrate is prepared by mixing the following substances:
  20 parts of active substance
  40 parts of ethyleneglycol monoethylether
  10 parts of N,N-dimethylformamide
  30 parts of xylene To this concentrate there is admixed a cutting oil in a concentration of 0.1%. Protection from microbiological deterioration is obtained thereby.

EXAMPLE V

A wettable powder is obtained by mixing the following substances:
  55 parts of active substance
  3 parts of polyethyleneoxide
  5 parts of ligninsulfonic acid
  20 parts of diatomaceous earth
  17 parts of clay The powder is suspended in water and can be sprayed on surfaces in order to inhibit fungal growth.

EXAMPLE VI (WOOD ROT TEST)

The active substance is dissolved in an appropriate organic solvent. The wood to be protected is treated by the dipping technique (European norm 113). Such concentration has to be chosen that 1 to 3 kg of active substance is available per m$^3$ of wood.

The treated wood is buried for 12 to 16 weeks in a compost soil at 29°±10° C. and 97% of relative air humidity. Thereafter the wood is washed in cold water and dried.

The treated wood shows a much better protection against attack by microorganisms living in the soil than untreated wood.

EXAMPLE VII (BROWN ROT TEST)

*Pinus sylvestris* wood blocks of 5×2.5×0.5 cm were autoclaved for 20 minutes, subsequently dried for 19.5 hours at 100°–110° C., allowed to cool in a desiccator and weighed (initial dry weight).

One ml of 0.125% solution of the test compound in a 1/1 methanol/water mixture is equally distributed over the wood block so that the final concentration in the wood is 2 kg a.i./m$^3$. Blocks treated with water and with 1/1 methanol/water are included as controls.

The blocks are allowed to dry in a laminar flow chamber. Evaporation of the solvent is performed in an oven at 50° C. for 3 hours.

The blocks are then transferred onto malt-agar Petri dishes which have been inoculated 8 days before with *Coniophora puteana*. Two blocks, treated with the same concentration of the active ingredient are placed on a small stainless steel frame in the Petri dish to allow contact with the aerial mycelium of the fungus and to avoid contact with the agar medium.

The blocks are exposed to fungal attack for 8 weeks at 25° C. They are then freed from adhering mycelium oven-dried for 19.5 hours at 100°–110° C. and dried. In the following table are given mean results obtained on 4 blocks.

| Treatment | mean weight loss in % |
|---|---|
| 1. Water | 28.05 |
| 2. 1/1 methanol/water | 30.45 |
| 3. compound (V) 2 kg/m$^3$ | 14.15 |
| 4. compound (VI) 2 kg/m$^3$ | 2.03 |

EXAMPLE VIII
(WHITE ROT TEST)

*Fagus sylvatica* wood blocks of 5×2×0.6 cm are oven-dried for 18 hours, cooled in a desiccator and weighed. The test blocks are laid down in a Petri dish bottom and placed in a vacuum desiccator. Pressure is reduced to 40 mbar with a suction pump. The blocks are impregnated with a test solution comprising 3000 or 1500 ppm of the active substance in 50% aqueous methanol through a tube leading to the Petri dish. When the blocks are well-covered vacuum is released, the Petri dish is removed from the desiccator and left for two hours in order to saturate the blocks. Control blocks are treated in the same manner with 50% aqueous methanol. The blocks are tamponed with filter paper, weighed and the amount of test compound taken up is calculated Four blocks are used for each compound and concentration.

The blocks are then sterilized by treating them 3 times for 5 minutes with steam of about 100° C. Six days after treatment the blocks are transferred to malt-agar Petri dishes which have been inoculated 20 days before with *Coriolus versicolor*. Two blocks, one treated and one control, are placed on stainless steel frame in the Petri dish.

The test blocks are exposed to fungal attack for 8 weeks at 25° C. In order to avoid desiccation the Petri dishes are put together in a plastic bag. The blocks are scored visually according to the following score system:
score 0=no attack
score 1=slight attack
score 2=moderate attack
score 3=severe attack The blocks are freed from adhering mycelium, oven-dried for 18 hours at 100°–110° C., allowed to cool in a desiccator and weighed.

The mean results obtained on 4 blocks each time are given in the following table.

| Treatment | Conc. a.i. in kg/m$^3$ wood | Weight loss in % | visual score |
|---|---|---|---|
| 1. Compound (V) | 1.93 | 0 | 0 |
| 3000 ppm control | — | 17 | 3 |
| 2. Compound (V) | 0.93 | 0 | 0 |
| 1500 ppm control | — | 19 | 3 |
| 3. Compound (VI) | 1.85 | 0 | 0 |
| 3000 ppm control | — | 20 | 3 |
| 4. Compound (VI) | 0.96 | 0 | 0 |
| 1500 ppm control | — | 16 | 3 |

What is claimed is:

1. A method of protecting wood products or wood product coatings from deterioration by microorganisms which comprises applying to or incorporating in said wood products or coatings an antimicrobially effective amount of at least one compound selected from the group consisting of an azole derivative having the formula

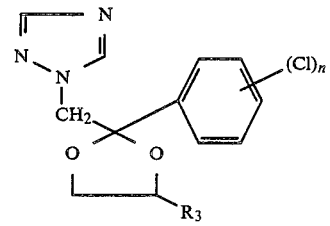

and the organic and inorganic acid addition salts thereof, where R$_3$ is hydrogen or C$_1$–C$_3$ alkyl and n is 1 or 2.

2. The method of claim 1 wherein

is 2,4-dichlorophenyl.

3. The method of claim 1 wherein said azole derivative is 1-[2-(2,4-dichlorophenyl)-4-methyl-1,3-dioxolan-2-ylmethyl]-1H-1,2,4-triazole.

4. The method of claim 1 wherein said azole derivative is 1-[2-(2,4-dichlorophenyl)-1,3-dioxolan-2-ylmethyl]-1H-1,2,4-triazole.

5. The method of claim 1 wherein said azole derivative is 1-[2-(2,4-dichlorophenyl)-4-ethyl-1,3-dioxolan-2-ylmethyl]-1H-1,2,4-triazole.

6. The method of claim 1 wherein said azole derivative is 1-[2-(2,4-dichlorophenyl)-4-propyl-1,3-dioxolan-2-ylmethyl]-1H-1,2,4-triazole.

* * * * *